US005677308A

United States Patent [19]

Lerner

[11] Patent Number: 5,677,308
[45] Date of Patent: Oct. 14, 1997

[54] METHOD FOR ALLEVIATING SPASMODIC TORTICOLLIS

[76] Inventor: A. Martin Lerner, 525 Harmon, Birmingham, Mich. 48009

[21] Appl. No.: 770,699

[22] Filed: Dec. 19, 1996

[51] Int. Cl.$^6$ ..................................................... A61K 31/52
[52] U.S. Cl. ............................................. 514/262; 514/261
[58] Field of Search ..................................... 514/262, 261

[56] References Cited

U.S. PATENT DOCUMENTS

| | | | |
|---|---|---|---|
| 4,493,328 | 1/1985 | Saito | 128/782 |
| 4,544,634 | 10/1985 | Krenitsky | 435/119 |
| 4,695,570 | 9/1987 | Krenitsky | 514/261 |
| 4,897,394 | 1/1990 | Zimmerman et al. | 514/258 |
| 4,957,924 | 9/1990 | Beauchamp | 514/262 |
| 5,061,708 | 10/1991 | Krenitsky | 514/262 |
| 5,079,252 | 1/1992 | Beauchamp | 514/262 |
| 5,206,248 | 4/1993 | Smith | 514/289 |
| 5,298,019 | 3/1994 | Borodic | 604/51 |
| 5,405,850 | 4/1995 | Blumenkopf | 514/262 |

OTHER PUBLICATIONS

"Selective Peripheral Denervation for Spasmodic Torticollis: Is the Outcome Predictable?", V. Braun, et al *J. Neurol* (1995) 242(8):504–507.

"Selective Peripheral Denervation for the Treatment of Spasmodic Torticollis" V. Braun, et al, *Neurosurgery*, vol. 35, No. 1, Jul., 1994, pp. 58–63.

"Clinical and Polymographic Investigation of Spasmodic Torticollis", G. Deuschl, et al, *Journal of Neurology*, vol. 239, pp. 9–15 (1992).

"Botulinum a Toxin for Spasmodic Torticollis: Multiple vs. Single Injection Points per Muscle", Gary E. Borodic, et al, *Head & Neck*, 14(1):33–7, Jan–Feb. 1992.

"Effectiveness of Botulinum Toxin in the Treatment of Spasmodic Torticollis", D. Boghen, et al, *European Neurology*, 33(3):199–203, 1993.

*International Pharmaceutical Abstracts* No. 3111836, pp. 2244–2245.

"Modification of Muscle Activity after BOTOX Injections in Spasmodic Torticollis" C. Martin, et al, *Annals of Neurology*, vol. 32, No. 3, Sep., 1992, pp. 411–412.

*Primary Examiner*—Russell Travers
*Attorney, Agent, or Firm*—Brooks & Kushman P.C.

[57] ABSTRACT

A method for alleviating spasmodic torticollis with the administration of antiviral agents. Based on clinical tests, spasmodic torticollis is a persistent herpes simplex virus infection and thus administration of antiviral agents has shown to alleviate the symptoms associated with the disorder. Based on therapeutic trials, patients receiving the recommended antiviral treatment, have experienced significant reduction or elimination of the abnormal tonic and clonic movements associated with ST.

12 Claims, No Drawings

METHOD FOR ALLEVIATING SPASMODIC TORTICOLLIS

TECHNICAL FIELD

This invention relates to a method for alleviating localized movement disorders, specifically spasmodic torticollis with the administration of antiviral agents.

BACKGROUND ART

Localized movement disorders such as spasmodic torticollis produce distorted movement in a distinct muscular group. With spasmodic torticollis the distortion is generally focused in the neck muscles.

Spasmodic torticollis (ST) is a neurological disorder that affects muscles of the neck causing cervical dystonia. Spasmodic torticollis is generally a chronic condition characterized by an abnormal head position and involuntary head movements. Persons afflicted with ST suffer from uncontrollable head tremors, jerks and spasms. In severe cases, the head may be forced to lie upon the shoulder. The persistent and involuntary nature of the condition is both painful and emotionally debilitating.

This condition afflicts three of every 10,000 people and thus approximately 80,000 people in the United States suffer from ST. Despite the number of people afflicted, prior studies have not been able to determine the etiology of the disorder. Medical science has until recently characterized the disorder as psychiatric in nature or an automatic dysfunction. However, conventional methods such as psychotherapy or physiotherapy have proven highly unsuccessful. To date, medical and surgical procedures used in the treatment of this condition have been of little value.

The primary characteristic of spasmodic torticollis is the sustained or intermittent, involuntary contractions of the muscles around the neck, which control the position of the head. As a result of the involuntary contractions, the head leans or turns to one side. In some cases, the head may also be pulled, forward or backward, or the person may experience shaking movements of the head or arms. These involuntary muscle spasms lead to abnormal postures, usually with a twisting component.

When spasmodic torticollis manifests itself in childhood, the disorder may involve many parts of the body, a condition known as "generalized dystonia". In contrast, when the involuntary muscle spasms begin in adult life, such spasms are generally focused on one part of the body, a condition known as "focal dystonia". An early indication of the disorder involves a slight rotation of the head to one side. As an example, a person suffering from ST may have difficulty maintaining his/her head in a straight position. In other instances, the person's head may turn involuntarily or the person may experience a slight tremor.

Spasmodic torticollis generally advances slowly over a period of two to five years. While the condition can manifest itself at any time, the symptoms often surface around age 40. In as many as 20% of the patients, spontaneous recovery may occur. However, after such apparent recovery, the patient generally goes into remission.

ST patients experience localized pain on one side of the body and often in one area. Such pain generally occurs on the side of the neck, back or in the shoulder affected by the muscular contortions. For certain patients, an arm or a hand on the affected side has tremors or cramping. Spasmodic torticollis generally does not affect any other regions of the body, and has no effect on the person's mental faculties.

Interestingly enough, the involuntary muscle spasms associated with spasmodic torticollis, while prevalent during the day, do not manifest themselves in a person's sleeping state and are often reduced during the early morning period. It is believed that emotional stress, menses, pregnancy, reading, simultaneous use of both hands, or walking can aggravate the tonic motion, sustained turning of the head to one side or the clonic motion, shaking movements of the head.

While there is a substantial amount of pain associated with this disorder, the physical pain is only compounded by the emotional toll placed on an ST sufferer. As a result of the involuntary muscle spasms, ST sufferers are frequently unable to lead what would be considered a normal life. Instead, ST sufferers are often forced to become reclusive and keep the pain and physical manifestations of the condition hidden.

To date, there has been no reliable treatment for spasmodic torticollis. Rather, the current treatments attempt to target individual symptoms rather than identifying the etiology of the condition and implementing a treatment for the condition as a whole.

One such treatment option, as described in U.S. Pat. No. 4,493,328, involves an electromyograph biofeedback device to inhibit spastic activity associated with the disorder. This invention discloses a device which provides a combination of an electrical shock and electromyograph biofeedback whenever the muscle tension of the neck surpasses a certain threshold. However, this device operates under the incorrect assumption that spasmodic torticollis can be treated through behavioral modification. Accordingly, the device fails to provide a long-term solution.

Another such treatment involves intramuscular botulinum toxin injections into the neck to block neuromuscular transmission and, in effect, paralyze the involved muscles. The botulinum toxin blocks neuromuscular conduction by binding to receptor sites on motor nerve terminals, and inhibiting the release of acetyl choline. Such treatment is detailed in the "Effectiveness of Botulinum Toxin in the Treatment of Spasmodic Torticollis" publication by Dan Baghen, M.D., Eur Neurol 1993; 33; 199–203. Botulinum toxin treatment usually requires an identification of the muscles responsible for the dystonic movement so that the toxin can be injected into the appropriate neck muscles. Accordingly, polymyographic investigation may be a prerequisite to isolate the problem muscle areas.

The following side effects are associated with botulinum toxin treatment: transient fatigue, dysphagia, neck weakness, hoarseness and localized pain. In addition, many patients who preliminarily respond to botulinum toxin therapy subsequently become non-responsive to the treatment. Accordingly, for many patients the botulinum injections simply constitute a preface to neurosurgery. One surgical technique which many ST patients have undergone, selective peripheral denervation, attempts to de-vascularize the spinal accessory nerves in the paravertebral area. Such treatments are both painful, unnecessarily dangerous, and fail to provide any long term treatment of the condition.

Accordingly, there is a genuine need for a method of treating the involuntary muscle spasms which accompany spasmodic torticollis with a reliable, and effective technique which then allows an ST sufferer to integrate back into the mainstream of society.

SUMMARY OF THE INVENTION

It would be desirable to provide a method for alleviating the conditions associated with spasmodic torticollis by administering antiviral agents to target the infection which causes the disorder. It would be further desirable to provide a treatment for spasmodic torticollis through oral administration of an antiviral drug without the need for neurosurgery or toxin injections. It would be yet further desirable to provide a long-term treatment approach for ST sufferers.

A method for alleviating spasmodic torticollis, has now been discovered, the inventive method including administering to a patient in need thereof, a therapeutically effective quantity of one or more pharmaceutically acceptable antiviral agents which reduce distorted motion in the patient. Preferably, the antiviral agent administered is valacyclovir, marketed under the trademark Valtrex® by the Burroughs Wellcome Company. Valacyclovir is the L-valyl ester of the antiviral drug, acyclovir, marketed under the trade name Zovirax® by the Burroughs Wellcome Company.

As defined herein, a "therapeutically effective" amount of an antiviral agent is the amount by which a patient's muscular spasms are reduced, postural control is regained and the associated pain decreased. In addition, the term "alleviating" as used throughout the specification refers to relieving or reducing the symptoms associated with spasmodic torticollis and/or elimination of those symptoms.

Likewise, the term "pharmaceutically acceptable antiviral agent" is defined to include those antiviral agents which, upon administration, have no deleterious effect on the patient. Thus, where a particular antiviral agent is unsuitable to an individual, that antiviral agent would not be pharmaceutically acceptable and would thus not be administered.

In patients tested to date who are suffering from spasmodic torticollis, administration of antiviral agents, was remarkably effective at reducing the abnormal tonic and clonic movements of the patient.

While not wishing to be bound to a particular explanation, based on the research conducted, spasmodic torticollis is understood to be a persistent infection caused by the herpes simplex virus, probably herpes simplex virus type one. Other members of the herpes virus family, for instance, varicella zoster, on occasion, may cause spasmodic torticollis. The research conducted further clarified the mechanism by which the herpes simplex virus produces the abnormal motor movement associated with spasmodic torticollis. Having determined the underlying cause of these disorders, clinical tests confirmed the effectiveness of antiviral agents in the treatment.

The amount of antiviral agent required to constitute a "therapeutically effective" amount will vary based on a number of factors including the severity of the spasmodic torticollis and the identity and chemical makeup of the patient.

In the preferred embodiment, the patient was administered valacyclovir 30 milligrams/kilogram of body weight of the patient (e.g. 2.0 grams) orally every six hours, a dosage chosen to approximate the pharmacokinetics of acyclovir at a dosage of ten milligrams/kilogram of body weight intravenously every eight hours. Following this preferred therapy, the patients tested to date resumed increasingly better postural control of the head and neck, with a decrease in the frequency and intensity of the neck muscle spasms. Pain in the neck and shoulder decreased and pain medicines were less frequently needed. The studies have shown that improvement is gradual and steady at 3–6 months after initiation of the valacyclovir treatment.

Various objects, features and advantages of the present invention are readily apparent from the following detailed description of the invention.

DETAILED DESCRIPTION OF THE INVENTION

Spasmodic torticollis is a disturbance of movement in postural control of the head and neck, often associated with abnormal head posture and involuntary head movements. Patients suffering from ST often suffer from severe neck posture deformity, including a position whereby the neck effectively rests on the shoulder, tremors and reduced range of neck movement and severe pain and discomfort associated with the abnormal posturing and movement. In general, spasmodic torticollis involves the scalene, sternocleidomastoid, and upper trapezius muscles.

To date, there has been no understanding of the underlying cause of spasmodic torticollis. As a result of this failure to understand the etiology behind the disorder, treatment options have failed to target the root of the problem.

In conducting examinations of spasmodic torticollis patients, the inventor observed that several of the patients experienced recurrent episodes of herpes simplex stomatitis affecting the hard palate, a very unusual place for recurrent oral labial herpes. Through further investigations it became evident that the administration of oral valacyclovir to treat the herpetic ulcerative lesions of the hard palate also resulted in a noticeable disappearance of the neck pain and associated internal posturing of the arm and hand, classic ST symptoms. As a result of the administration of oral valacyclovir, further tests were conducted to determine what, if any, relationship exists between spasmodic torticollis and the herpes simplex virus (HSV). Moreover, clinical trials were conducted to determine whether spasmodic torticollis is a persistent infection due to the herpes simplex virus.

Research and clinical efforts led to the surprising and singular conclusion, that spasmodic torticollis constitutes a persistent infection caused in most instances by the herpes simplex virus, probably herpes simplex virus type one. Research also assisted in uncovering the mechanism through which the herpes virus is believed to attack the specific muscles afflicted with spasmodic torticollis. Clinical trials then confirmed the efficacy of antiviral agents in the treatment of the disorder.

It is believed that individuals with ST were exposed to the herpes virus in the oropharynx region during initial primary infection. During primary infection, as the body has no antibodies or specific cell-mediated immunity to HSV, the virus travels through the sensory or motor nerves of the muscles and mucosa of the pharynx and/or to a latent site in the motor ganglia. More specifically, the virus travels up the associated pharyngeal nerves to the cervical spinal cord. Pathways of the vagus, glossopharyngeal and sympathetic trunk by way of the pharyngeal plexus may be involved. Once the virus has established a latent site, the virus can travel via the motor nerves back and forth from this site via neural pathways to the muscles affected by the spasmodic torticollis disorder. Herpes simplex virus is known to travel along neural pathways by means of the axon of the affected nerve.

It is believed that the herpes simplex virus produces the motor abnormal movement syndrome of spasmodic torticollis just as it causes the sensory paralytic syndrome of Bell's palsy. Under this theory, it is believed that the herpes simplex virus widely affects the epithelium of the pharynx and perhaps the nose during the primary infection of the herpes simplex virus Type-1. Following primary infection, the virus is believed to access the brain and spinal cord via the sensory nerves which are open, naked axons as syncytia in the epithelium of the pharynx. The virus then travels along the nervous axon, which guides the virus to the brain. For instance, the pharynx sensory fibers come from the trigeminal nerve (5th cranial nerve) via the pterygopalatini nerve. Likewise, sensory fibers of the pharynx come from the glossopharyngeal nerve, the ninth cranial nerve.

The sensory axons are accessible at the surface of the throat and the pharynx via the epithelium or mucosa. The fibers of the sensory axons then gain access to the cervical cord via the ample pathways at the posterior column of the spinal cord and via the reticular substance, to form an arc to reach the motor nerves of the sternocleidomastoid muscle which bends the cervical vertebral column laterally, and draws the head to the shoulder ipsilaterally, and rotates the head pointing the chin upward and to the opposite side. This movement involves cervical nerves 2 and 3. Likewise, the scalenus anterior muscle innervates cervical nerves 6 and 7. Similarly, the trapezius muscle rotates and adducts the scapula. The trapezius muscle is served by cervical nerves 3 and 4, the scalenus anterior muscle by cervical nerves 6 and 7, and the sternocleidomastoid by cervical nerves 2 and 3. These three muscles, the trapezius, the sternocleidomastoid and the scalenus anterior muscle are the major muscles involved in the movement of the neck and head experience abnormal movements from the spasmodic torticollis disorder. The trigeminal nerve may, likewise, be reached by this pharyngeal sensory nerve pathway in the reticular system of the brain stem to reach sensory nerves of the fifth cranial nerve. Thus, it is believed that a single mechanism explains the link between the herpes virus and spasmodic torticollis.

Herpes simplex viruses are characterized by several key properties: (1) their role as a significant pathogen responsible for a variety of diseases; (2) the ability of the herpes virus to remain latent in their host for life, and to be reactivated at or near the site of initial infection; and (3) to multiply efficiently and irreversibly destroy the cells that they infect. The herpes simplex virus enters sensory nerves innervating the cells of mucosal membranes. In latently infected neurons, the viral genome acquires the characteristics of endless or circular DNA and may be a nucleosoma form. It is believed that, in a fraction of neurons harboring latent herpes simplex virus (HSV), the virus is periodically reactivated. Infectious viruses carry back to peripheral tissues by axonal transport, usually to cells at or near the site of initial infection.

The herpes virus must come in contact with mucosal surfaces or abraded skin for infection to be initiated. After viral replication at the site of primary infection, either an intact virion or the capsid is transported by neurons to the dorsal root ganglia where after another round of viral replication, latency is established. Transport of the virion is by retro-grade axonal flow. The fundamental principles of the pathogenesis of herpes virus infections are the propensity of the virus to replicate at mucosal surfaces, to be transported to dorsal root ganglia, and after replication at that site, to become latent. After latency is established, reactivation will occur with proper stimulus, and the virus will manifest itself at mucocutaneous sites. Occasionally, with primary infection, the virus may spread beyond the dorsal root ganglia and cause systemic infection. It is believed that widespread organ involvement is a consequence of viremia in a host not capable of limiting replication to mucosal surfaces.

Both histopathologic and electron microscopic studies have conclusively shown axonal transport as the means for translocation of the virus from a peripheral site to a central site. Transport of the capsid containing viral DNA via sensory nerves to central axons occurs at a rate of approximately 10 mm/hour. Following transport, the virus replicates for several days in the associated sensory ganglia that innervates the sites of inoculation. In the latent state, once replication in the sensory ganglia is complete, antiviral drugs have no effect on the virus. It is thus believed that the latent virus does not multiply and therefore the antiviral agents have no effect on the virus in its latent form.

Infection with herpes simplex Type 1, generally limited to the oropharynx, can be transmitted by respiratory droplets or through direct contact of a susceptible individual with infected secretions. Thus, initial replication of the virus will occur in the oropharyngeal mucosa, followed by the establishment of a latent infection in cells of the trigeminal ganglia. Certain individuals appear to have a genetic predisposition and are more susceptible to the herpes virus.

While it is known that antiviral agents are effective in the treatment of viral infections, there are a number of problems associated with such antiviral agents. As the herpes simplex viruses are intracellular parasites which use multiple biochemical pathways of the infected host cell, there are problems associated with achieving clinically useful antiviral activity without also adversely affecting metabolism of the normal host cell.

As a selective inhibitor of herpes virus application, acyclovir represents an important advance in antiviral therapy. Acyclovir was synthesized in 1974 by Beauchamp and Schaeffer of Burroughs Wellcome Company. Acyclovir, 9-((2-hydroxyethoxy) methyl) guanine E, demonstrated significant in vitro antiviral activity against herpes viruses, specifically, HSV and varicella zoster virus (VZV).

Acyclovir is an acyclic analogue of guanosine. The inhibitory activity of acyclovir is highly selective. The enzyme thymidine kinase (TK) of normal uninfected cells does not effectively use acyclovir as a substrate. However, TK encoded by the herpes simplex virus converts acyclovir into acyclovir monophosphate, a nucleotide analogue. The monophosphate is further converted into diphosphate by cellular guanylate kinase and into triphosphate by a number of cellular enzymes. Acyclovir triphosphate interferes with herpes simplex virus DNA polymerase and inhibits viral DNA replication. Acyclovir is preferentially taken up and selectively converted to the active triphosphate form by herpes virus-infected cells. Acyclovir triphosphate binds viral DNA polymerase, acting as a DNA chain terminator. Because acyclovir is taken up selectively by virus-infected cells, the concentration of acyclovir triphosphate is 40 to 100 times higher in infected cells than in uninfected cells. Furthermore, viral DNA polymerase exhibits a 10 to 30-fold greater affinity for acyclovir triphosphate than do cellular DNA polymerases. The higher concentration of the active triphosphate metabolite in infected cells plus the affinity for viral polymerases results in the very low toxicity of acyclovir for normal host cells.

Acyclovir is available in ointment, capsule and intravenous formulations. Oral acyclovir or more recently valacyclovir or other similar anti-viral drugs is indicated in the management cases of primary or initial genital herpes in all patient populations and as long-term suppressive therapy in normal adults with frequently recurrent genital herpes. Oral acyclovir also is used for prophylaxis and treatment of immunocompromised patients with a history of clinical evidence of an active HSV infection. Intravenous acyclovir is used in the treatment of severe primary or initial herpes genitalis of immunocompetent patients, some initial and recurrent mucocutaneous HSV infections in immunocompromised patients, neonatal HSV infections and herpes simplex virus encephalitis in infants, children and adults.

In addition, acyclovir has an excellent safety profile and is well-tolerated by most patients. The major adverse effect of acyclovir is alteration of renal function. Adequate hydration of patients can prevent renal concretion of drug as it is eliminated by the kidney preventing renal dysfunction.

More recently, Burroughs Wellcome has introduced Valtrex® (valacyclovir hydrochloride) the hydrochloride salt of L-valyl ester of acyclovir. Valacyclovir hydrochloride is L-valine, 2-[(2-amino-1, 6-dihydro-6-oxo-9H-purin-9-yl) methoxy]ethylester, monochloride. Valacyclovir has the molecular formula $C_{13}H_{20}N_6O_4 \cdot HCl$, a molecular weight of 360.80 and the following structural formula:

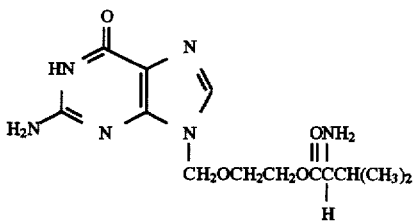

Valacyclovir hydrochloride has a maximum solubility in water at 250° C. of 174 mg/ml.

After oral administration, valacyclovir is rapidly absorbed from the gastrointestinal tract. Valacyclovir is nearly completely converted to acyclovir and an L-valine by first-path intestinal and/or hepatic metabolism. Valacyclovir is rapidly converted to acyclovir, which has in vitro and in vivo inhibitory activity, against herpes simplex virus Types 1 (HSV-1) and 2 (HSV-2) and varicella-zoster virus (VZV). Of these latter three herpes viruses, acyclovir has highest antiviral effectiveness against herpes simplex virus type 1. The inhibitory activity of acyclovir is highly selective due to its affinity for the enzyme thymidine kinase (TK) and encoded by HSV, VZV and Epstein-Barr virus (EBV). Thymidine kinase converts acyclovir into acyclovir monophosphate, a nucleotide analog. The monophosphate is further converted into diphosphate by cellular guanylate kinase and into triphosphates, a finite number of cellular enzymes. In vitro, acyclovir triphosphate stops replication of herpes viral DNA. This is accomplished in three ways: (1) competitive inhibition of viral DNA polymerase; (2) incorporation and termination of the growing viral DNA chain; and (3) inactivation of the viral DNA polymerase. The greater antiviral activity of acyclovir against HSV compared to VZV is due to its more efficient phosphorylation by the viral thymidine kinase (TKN). The bioavalibility of acyclovir after administration of valacyclovir is 54.5% ±9.1% as determined following a one gram oral dose of valacyclovir and a 350 milligram intravenous acyclovir dose.

Valacyclovir is the preferred antiviral agent due to its relatively high bioavailability. As a result of valacyclovir's increased absorption, as compared to acyclovir for example, less frequent, smaller total dosages of valacyclovir are required to reach effective antiherpetic levels.

The antiviral agent can be administered by any method appropriate, including oral, rectal, nasal, topical, vaginal and parenteral, including subcutaneous, intramuscular, intravenous, intradermal, intrathecal and epidural. The preferred method is oral.

The amount of antiviral agent required to constitute a "therapeutically effective" amount will vary based on a number of factors including the severity of the spasmodic torticollis and the identity and chemical makeup of the patient.

In general, to provide a therapeutically effective amount of the antiviral agent, a suitable effective dose will be in the range of 0.1 to 25 grams per day and preferably in the range between two grams to 20 grams per day. An optimum dose is about 5–15 grams per day. The dosage of course varies with the body weight of the patient and so for a 70 kilogram individual a dose of 8 grams is optimum. In view of toxicity considerations, a maximum dose for a 70 kilogram individual is 12 grams per day. The desired dose is preferably presented as 2, 3, 4 or more smaller doses administered at appropriate intervals throughout the day. These smaller doses may be administered in unit dosage forms.

In particular for valacyclovir, a patient would be administered a dosage in the range of 0.1 milligrams/kilogram body weight of the patient to 50 milligrams/kilogram of body weight of valacyclovir hydrochloride per dosing interval, generally every six hours. The dosing interval is determined by the bioavailability of the antiviral agent in nervous tissue and its excretion from the body. In the preferred embodiment, the patient would be administered a dosage in the range of 10–40 milligram/kilogram of body weight valacyclovir hydrochloride orally every six hours. In the most preferred embodiment, a patient would be administered 30 milligrams/kilograms of body weight of valacyclovir hydrochloride every six hours. These dosage ranges were selected to approximate the pharmacokinetics of intravenous acyclovir, at a dosage schedule of 10 milligrams/kilograms of body weight every 8 hours, intravenously.

While valacyclovir is the preferred antiviral agent, other antiviral agents which demonstrate antiherpetic action may be used for the treatment of spasmodic torticollis as well. Such antiviral agents may also be effectively administered, e.g., by oral methods, or as larger doses in time delay formulations, etc. Included among this group of antiviral agents are acyclovir, ganciclovir, valacyclovir, famciclovir, cidofovir, and other herpetic antiviral agents, and pharmaceutically acceptable derivatives of these antiviral agents. Such pharmaceutically acceptable derivatives include salts, hydrolyzable esters, and chelates of the antiviral agents and such similar derivatives which have no negative pharmaceutical effect on the patient upon administration and are thus "pharmaceutically acceptable". A pharmaceutically acceptable salt is preferably an acidic salt derived from an appropriate acid, for example, hydrochloric, sulfuric, phosphoric, maleic, fumaric, citric, tartaric, lactic, acetic or p-toluenesulphonic acid. Particularly preferred salts are the hydrochloride salts.

Another antiviral agent, ganciclovir, is also effective in the treatment of HSV infections. Like acyclovir, the activity of ganciclovir in HSV-infected cells depends on phosphorylation by virus-induced TK. Like acyclovir, ganciclovir monophosphate is further converted to its di- and triphosphate derivatives by cellular kinases. In cells infected by HSV-1 or HSV-2, the triphosphate competitively inhibits the incorporation of guanosine-TP into viral DNA. The triphosphate is incorporated at internal and terminal sites of viral DNA, thus inhibiting DNA synthesis.

Another effective antiviral agent is Vistide®, or cidofovir, 1-[(s)-3-hydroxy-2-(phosphonomethoxy)propyl]cytosine dihydrate with the molecular formula of $C_8H_{14}N_3O_6P\cdot2H_2O$ and a molecular weight of 315.22. Cidofovir again suppresses replication of the herpes virus by selective inhibition of viral DNA synthesis. Cidofovir is incorporated into the growing viral DNA chain which results in reductions in the rate of viral DNA synthesis.

Famvir™, famciclovir also has antiviral activity against herpes virus 1. Famciclovir is 2-[2-(2-amino-9H-purin-9-yl) ethyl]-1, 3-propanediol diacetate. With a molecular formula of $C_{14}H_{19}N_5O_4$ and a molecular weight of 321.3. Famciclovir undergoes rapid biotransformation to the active antiviral compound penciclovir, which has inhibitory activity against herpes simplex virus types 1 and 2 and varicella zoster virus (VZV).

Famciclovir is the diacetyl 6-deoxy analog of the active antiviral compound penciclovir. The absolute bioavalibility of famciclovir is 77±8%, as determined from the administration of a 500 mg famciclovir oral dose and a 400 mg penciclovir intravenous dose. In herpes simplex virus 1 and herpes simplex virus 2, viral thymidine kinase phosphorylates penciclovir to its monophosphate form which, in turn, is converted to penciclovir triphosphate by cellular kinases.

In an effort to diagnose herpes simplex, standard neurodiagnostic procedures are used in the evaluation of patients and include cerebrospinal fluid examination, EEG, and one or more scanning procedures, such as technetium, CAT, or MRI. Characteristic abnormalities of the cerebrospinal fluid include pleocytosis, usually mononuclear cells, and elevated protein. On serial cerebrospinal fluid examination, protein concentration and cell counts virtually always increase dramatically. This observation is helpful in distinguishing herpes simplex virus infection of the central nervous system from other viral infections. However, the symptoms of ST are well known and its diagnosis straight forward.

Having generally described this invention, a further understanding can be obtained by reference to certain specific examples which are provided herein for purposes of illustration only and are not intended to be limiting unless otherwise specified.

EXAMPLES

The present inventor has analyzed the effectiveness of various antiviral agents as a method of treatment for patients having localized movement disorders for several years. As a result of these patient trials, it was found that administration of antiviral agents, over a brief period of time, contributed to a significant improvement in the clinical symptoms and signs and to the improvement toward normalization of the movement disorder.

In an initial therapeutic trial, three patients were treated with valacyclovir. One of these patients, a 43-year old woman with a history of spasmodic torticollis for 2-½ years, while otherwise healthy, experienced severe pain in the neck and a pulling of the neck to the left. Following a normal CAT scan of the brain, a lumbar puncture was done. During this test, the cerebrospinal fluid surprisingly showed a pleocytosis of 100 lymphocytes/mm³. The lumbar puncture test thus was consistent with a cervical radiculitis as postulated. Using the polymerase chain reaction, the spinal fluid tested positive for herpes simplex virus type 1 nucleic acid.

Following this definitive determination of herpes simplex virus 1 infection, the patient was administered valacyclovir two grams orally every six hours. This dosage was chosen to approximate the pharmacokinetics of acyclovir at a dosage of 10 milligrams/kilogram intravenously every 6 hours. The patient continues with this dose for 3-½ months post-therapy. As a result of the administration of the valacyclovir, the patient's head was no longer prostrated on her shoulder but was rather at a 45° angle and the abnormal tonic and clonic movements considerably reduced.

The second patient, a 57-year old woman, suffered from ST for twelve years. The patient was receiving injections of botulinum toxins every three months. However, the beneficial temporary effects of the botulinum toxin were decreasing. Moreover, the patient as a result of her position and the intermittent tonic and clonic movements, became a social recluse. Following the administration of oral valacyclovir (2 grams every 6 hours), the patient no longer requires botulinum toxin and her tremors have considerably reduced. Neck and shoulder pain remains less as well. This patient is continuing her valacyclovir dosages.

A third patient is a 46-year old male whose ST first manifested itself in 1993. This patient has received botulinum toxin treatments. The patient's head is positioned far to the left and is often frequently lying horizontal on his left shoulder. As a result of this strained muscular position, severe pain was associated with the disorder. This patient has been given similar dosages of valacyclovir, and following a three-month administration, the response has been remarkable. The patient's head is now completely upright, and while he has slight residual head movement to the left, there are long periods during which the patient's head is in a normal upright position. Moreover, the severe pain associated with the disorder is dramatically reduced.

In all three patients, no further botulinum toxin treatment has been required.

While the foregoing treatments have involved administration of valacyclovir, the test results and results of treatment are entirely consistent with the postulate that ST is caused by a persistent herpes virus infection, particularly an infection of the family of herpes microorganisms, and therefore, treatment by other antiviral agents which demonstrate anti-herpetic action may be used for treatment of ST as well. Included among this group of antiviral agents are acyclovir, ganciclovir, valacyclovir, famciclovir, cidofovir, pharmaceutically acceptable derivatives and mixtures thereof and other herpetic antiviral agents used in concentrations which achieve adequate antiviral levels in the cerebrospinal fluid and nerve tissue including the brain.

While the best mode for carrying out the invention has been described in detail, those familiar with the art to which this invention relates will recognize various alternative ways of performing the invention as defined by the following claims.

What is claimed is:

1. A method for alleviating spasmodic torticollis in a patient, comprising:

administering to the patient in need thereof, a therapeutically effective amount of one or more pharmaceutically acceptable antiviral agents.

2. The method of claim 1 wherein the one or more antiviral agents are selected from the group consisting of acyclovir, ganciclovir, valacyclovir, famciclovir, cidofovir, and pharmaceutically acceptable derivatives and mixtures thereof.

3. The method of claim 1 wherein the patient is administered 0.1 to 25 grams of the one or more antiviral agents per day.

4. The method of claim 1 wherein the patient is administered 2 to 20 grams of the one or more antiviral agents per day.

5. The method of claim 1 wherein the patient is administered 5 to 15 grams of the one or more antiviral agents per day.

6. The method of claim 1 wherein the one or more antiviral agents are administered orally.

7. The method of claim 1 wherein the one or more antiviral agents are administered intravenously.

8. The method of claim 1 wherein the one or more antiviral agents are valacyclovir hydrochloride.

9. The method of claim 8 wherein the patient is administered 0.1 to 50 milligrams of valacyclovir hydrochloride per kilogram of body weight of the patient every six hours.

10. The method of claim 8 wherein the patient is administered 10 to 40 milligrams of valacyclovir hydrochloride per kilogram of body weight of the patient every six hours.

11. The method of claim 8 wherein the patient is administered 30 milligrams of valacyclovir hydrochloride per kilogram of body weight of the patient every six hours.

12. A method for alleviating spasmodic torticollis in a patient, comprising:

administering to a patient in need thereof, a therapeutically effective amount of one or more pharmaceutically acceptable antiviral agents, wherein the one or more antiviral agents are selected from the group consisting of acyclovir, ganciclovir, valacyclovir, famciclovir, and cidofovir and pharmaceutically acceptable derivatives and mixtures thereof.

* * * * *